United States Patent
Tilney

(10) Patent No.: US 11,576,850 B1
(45) Date of Patent: Feb. 14, 2023

(54) FACE PEEL FORMULATION AND METHOD OF APPLICATION

(71) Applicant: PLATINUM SKIN CARE INC., Clinton Township, MI (US)

(72) Inventor: Jennifer Tilney, Chesterfield Township, MI (US)

(73) Assignee: Platinum Skin Care, Inc., Clinton Township, MI (US)

( * ) Notice: Subject to any disclaimer, the term of this patent is extended or adjusted under 35 U.S.C. 154(b) by 75 days.

(21) Appl. No.: 17/142,724

(22) Filed: Jan. 6, 2021

Related U.S. Application Data

(60) Provisional application No. 62/957,564, filed on Jan. 6, 2020.

(51) Int. Cl.
| | |
|---|---|
| *A61K 36/00* | (2006.01) |
| *A61K 8/67* | (2006.01) |
| *A61K 8/9789* | (2017.01) |
| *A61K 8/31* | (2006.01) |
| *A61K 8/92* | (2006.01) |
| *A61K 8/37* | (2006.01) |
| *A61K 8/34* | (2006.01) |
| *A61Q 19/08* | (2006.01) |
| *A61Q 19/00* | (2006.01) |
| *A61Q 19/02* | (2006.01) |
| *A61K 8/49* | (2006.01) |

(52) U.S. Cl.
CPC ............ *A61K 8/676* (2013.01); *A61K 8/31* (2013.01); *A61K 8/347* (2013.01); *A61K 8/375* (2013.01); *A61K 8/4973* (2013.01); *A61K 8/671* (2013.01); *A61K 8/678* (2013.01); *A61K 8/92* (2013.01); *A61K 8/9789* (2017.08); *A61Q 19/004* (2013.01); *A61Q 19/02* (2013.01); *A61Q 19/08* (2013.01); *A61K 2800/28* (2013.01)

(58) Field of Classification Search
CPC ..... A61K 8/676; A61K 8/671; A61K 2800/28
See application file for complete search history.

(56) References Cited

U.S. PATENT DOCUMENTS

| | | |
|---|---|---|
| 5,516,793 A | 5/1996 | Duffy |
| 6,180,133 B1 | 1/2001 | Quan et al. |
| 6,521,237 B2 | 2/2003 | Cole et al. |
| 6,967,217 B1 | 11/2005 | Zucchetti et al. |
| 8,178,113 B2 | 5/2012 | Abdullah |
| 9,155,915 B2 | 10/2015 | Kunin |
| 9,468,597 B1 | 10/2016 | Perry |
| 9,636,292 B2 | 5/2017 | Sweeney et al. |
| 10,052,468 B1 | 8/2018 | Rodan et al. |
| 2003/0211126 A1 | 11/2003 | Fitzpatrick et al. |
| 2003/0232091 A1 | 12/2003 | Shefer et al. |
| 2004/0136938 A1 | 7/2004 | Ladislas et al. |
| 2006/0263398 A1 | 11/2006 | Kalil |
| 2008/0057138 A1 | 3/2008 | Telford et al. |
| 2013/0074860 A1 | 3/2013 | Colvan et al. |
| 2019/0091114 A1* | 3/2019 | Choi ................. A61K 8/44 |

OTHER PUBLICATIONS

Regenerating 5% Retinol Gel Truth Treatment Systems; © 2020 Benjamin Knight Fuchs; Retrieved from the Internet: <URL: www.truthtreatments.com.
Retinol_Lactic 10_10—Dermodality Skin Solutions; © 2020 Dermodality Skin Solutions; Retrieved from the Internet: <URL: www.dermodality.com>.

* cited by examiner

*Primary Examiner* — Qiuwen Mi
(74) *Attorney, Agent, or Firm* — Gregory Ozga; Warn Partners, P.C.

(57) ABSTRACT

A method of applying a skin peel formulation or product that includes providing a skin peel formulation or product containing at least 10% of the total weight of the skin peel formulation or product being vitamin A. Also provided is vitamin C present in at least 20% of the total weight of the skin peel formulation or product, wherein the vitamin C is in oil soluble form. The skin peel formulation is applied to a region of the body without any acid pre-treatments. After application of the skin peel formulation the user waits at least 25 days before reapplying the skin peel formulation again.

16 Claims, No Drawings

FACE PEEL FORMULATION AND METHOD OF APPLICATION

CROSS-REFERENCE TO RELATED APPLICATION

This application claims the benefit of U.S. Provisional Application No. 62/957,564; filed Jan. 6, 2020. The disclosure of the above application is incorporated herein by reference.

FIELD OF THE INVENTION

The present invention relates to a face peel formulation or product that is able to exfoliate the outer skin layer of the face or body and provide moisture that eases skin irritation during the peeling process.

BACKGROUND OF THE INVENTION

There are currently several skin peel formulations or products out on the market today. Most formulations use acids that are used to exfoliate or "peel" the skin layers away. The active ingredient used in such formulations can take many forms including phenolic acid, lactic acid, glycolic acid, mandelic acid, salicylic acid and an acid form of vitamin A called retinol. Typical skin peel formulations using retinol are used daily and exfoliate the outer layers of the skin over a long period of time. The retinol content of these formulations is often quite low in a range of 1% to 5% of the total volume of the formulation. The low percentage of vitamin A is necessary to make the product suitable for daily use and also to prevent unwanted irritation of the skin that occurs when greater percentages of vitamin A are present. While vitamin A is a desirable for use in skin peel formulations, use in greater percentage has resulted in unwanted or painful exfoliation of the skin. Where formulations having greater percentages of vitamin A are used, they typically are not single use applications and are used in connection with other skin peel formulations.

It is an object of the invention to provide a formulation that is designed for monthly use, that will effectively exfoliate the skin. It is further desirable to provide a formulation that will protect the skin from too much irritation during the exfoliation process. It is further desirable to provide a skin peel formulation that acts faster than that of known skin peel formulations, reduces pain and discomfort, but can be applied without any pre-treatments apart from water.

SUMMARY OF THE INVENTION

The present disclosure provides a skin peel formulation including a plurality of substances, such as an exfoliants in the form of Vitamin A and a moisturizer in the form of an oil based Vitamin C. In one embodiment the Vitamin A is an all-trans-retinol in caprylic/capric triglyceride with a 1% butylated hydoxytoluene (BHT) stabilizer sold in lipid base is commercially available from BASF Corporation, 100 Park Avenue, Florham Park, N.J. 07932 USA. The other main component is Vitamin C which is in the form of tetrahexyldecyl ascorbate in oil based. Further, the skin peel formulations of the present invention contain retinol in the total weight amount greater than 5% for a very superficial peel to as high as at least 20% for a superficial peel.

In one embodiment of the invention provided herein is a method of applying a skin peel formulation or product. The method includes providing a skin peel formulation or product containing at least 10% of the total weight of the skin peel formulation or product being vitamin A. Also provided is vitamin C present in at least 20% of the total weight of the skin peel formulation or product, wherein the vitamin C is in oil soluble form.

The next step involves applying the skin peel formulation to a region of the body by first applying water to the region of the body, and then applying the skin peel formulation. This step of applying the skin peel formulation is done without any acid pre-treatments to the region of the body. The acid solutions that are not applied include any acid or combination of acids that sufficiently exfoliate the superficial dermis and/or epidermis. The acidic solution not applied can contain one or more of lactic acid, salicylic acid, resorcinol, glycolic acid, malic acid, mandelic acid, citric acid, Trichloroacetic acid (TCA), phenol, tartaric acid, Isoceteth-20, or a combination thereof. The region of the body is typically the face or neck area but can be any area of the body where skin peeling is desired.

The next step includes waiting at least 25 days before applying the skin peel formulation again to the region of the body without any pre-treatment to the region of the body. The skin peel formulation of the present invention in one embodiment uses a single application method and does not require daily application or pre-treatments with other substances, aside from water, which is optional, prior to applying the skin peel formulation. In another method of the invention the step of applying the skin peel formulation further includes repeating the step of applying the skin peel formulation for not more than 3 successive days prior to the step of waiting at least 25 days. This particular method is used when a deeper exfoliation of the skin is desired or if a user has a particular skin type that needs a greater dosage of the skin peel formulation to achieve the desired exfoliation.

In the various examples below the retinol content of the total weight of the skin peel formulation is present in various ranges including 5% to 10%, 6% to 11%, 6% to 12%, 8% to 13%, 10% to 15%, 5% to 20%, and 10% to 20%. Also, in the examples vitamin C in the form of tetrahexyldecyl ascorbate in oil form is used, wherein the tetrahexyldecyl ascorbate content of the total weight of the skin peel formulation is present in various amounts and ranges including about 15%, about 10% to about 30%, about 20% to about 30%, about 25% to about 30% and about 26%.

Also, in the various examples and embodiments of the invention the skin peel formulation includes additional components such as capric/caprylic triglyceride, *Helianthus annus* (sunflower) seed oil, *Persea gratissima* (avocado) oil, dimethyl isosorbide, *Macadamia ternifolia* seed oil, rosa moschata seed oil, *Rosmarinus officinalis* (rosemary) leaf extract, BHT, and tocopherol. Additionally, the skin peel formulations in the examples below contain *Sesamum indicum*, which is commercially available as a product called Linefill™, sold by Centerchem, inc., 20 Glover Avenue, Norwalk, Conn. 06850. In some examples the *Sesamum indicum* is present in the skin peel formulation in at least 3% of the total weight of the skin peel formulation. Also, in some examples the skin peel formulation further includes at least 1% of the total weight of the skin peel formulation being squalane, while other examples include providing at least 5% of the total weight of the skin peel formulation being vita oil. In some of the examples the vita oils include *Helianthus annus* (sunflower) seed oil, *Persea gratissima* (avocado) oil.

The methods of the present invention provide a user with the benefit of an exfoliation process that does not require acid pre-treatment or any type of pre-treatment. The benefits can be provided with a single use and reapplication is not necessary for at least 20 days. The method has been found to improve overall photodamage, fine lines and wrinkles, and skin tone unevenness. Improvement in skin after treatment with retinols as described herein in such methods can be, for example, at least 1.5 fold, at least 2-fold, at least 3-fold, at least 4-fold, at least 5-fold or more compared to untreated skin.

DETAILED DESCRIPTION OF THE PREFERRED EMBODIMENTS

The following description of the preferred embodiments are merely exemplary in nature and are in no way intended to limit the invention, its application, or uses.

All percentages and ratios used herein are by total weight of the skin peel concentration and all measurements made at 25° C. or room temperature, unless otherwise designated. All percentages are on a weight/weight basis.

The term "about" means a range of values including the specified value, which a person of ordinary skill in the art would consider reasonably similar to the specified value. In certain embodiments "about" means within a standard deviation using measurements generally acceptable in the art.

As used herein the term "face peel formulation" or "face peel formulations" refer to a composition(s) or product(s) useful for topical application to the skin of a human.

As used herein, the term "topical application" means to apply or spread the compositions to the surface of the skin.

As used herein, the term "cosmetically acceptable" means that the compositions or components thereof so described are of sufficiently high purity and suitable for use in contact with human skin without undue toxicity, incompatibility, instability, allergic response, and the like.

As used herein the word "treat," "treating" or "treatment" refers to using the compositions of the present disclosure prophylactically to prevent outbreaks of undesirable dermatological symptoms, or therapeutically to ameliorate an existing undesirable dermatological condition, and/or extend the duration of the aesthetic benefit of a chemical peel procedure or reduce the frequency of repeated chemical peel procedures.

The terms "effective amount" or "effective amounts", as used herein, mean an amount sufficient to provide a cosmetic benefit following one or more treatments.

Vitamin A in the form of Retinol has been shown to be useful in treating skin disorders such as acne and has also been used to reduce the appearance of wrinkles and aging in the skin due to prolonged sun exposure. Retinol causes exfoliation of outer layers of skin upon treatment and when used in high concentrations greater than 4% can cause a sunburn like sensation at the treatment area. The compositions of the present disclosure are useful in reducing fine wrinkles and lines, reducing pore size, exfoliating the skin, reducing, or eliminating acne, toning the skin, enhancing the skin's radiancy, and providing softer, smoother skin with a more uniform appearance, while also containing soothing compounds that help resolve the unwanted burning sensations experienced at the treatment site.

In one embodiment the present invention is directed to various skin peel formulations all having a high percentage of vitamin A and vitamin C. The vitamin A is in an acid form known as retinol. The amount of vitamin A used is present in various percentages of the total volume of the formulation. The formulation includes vitamin A of greater than or equal to 5%, about 5% to about 20%, about 5% to about 15%, about 6% to about 12%, about 9% to about 11% and preferably about 10% vitamin A.

The vitamin C used is an oil soluble form of vitamin C, such as but not limited to tetrahexyldecyl ascorbate. The formulation includes vitamin C of greater than 15%, about 10% to about 30%, about 20% to about 30%, about 25% to about 30% and preferably about 26%.

The formulation includes other general components including, but not limited to Linefill™, squalane, and vita oils. Additionally, the formulation contains specific components including, but not limited to capric/caprylic triglyceride, tetrahexyldecyl ascorbate, retinol, *Helianthus annus* (sunflower) seed oil, persea gratissima (avocado) oil, dimethyl isosorbide, *Sesamum indicum*, macadamia ternifolia seed oil, squalane, rosa moschata seed oil, *Rosmarinus officinalis* (rosemary) leaf extract, BHT, and tocopherol.

SKIN PEEL FORMULATION EXAMPLES

Example 1-5% Vitamin a and 20% Vitamin C

A first sample of a skin peel formulation is prepared using cosmetically acceptable components, where the skin peel formulation includes at least 5% vitamin A and at least 20% vitamin C in oil soluble form. The vitamin A is in the form of retinol, while the vitamin C is tetrahexyldecyl ascorbate in oil soluble form. The remaining weight percentage of the sample include effective amounts of the following: effective amounts of vita oils including *Helianthus annus* (sunflower) seed oil, *Persea gratissima* (avocado) oil, capric/caprylic triglyceride, dimethyl isosorbide, *Sesamum indicum, Macadamia ternifolia* seed oil, rosa moschata seed oil, squalane, *Rosmarinus officinalis* (rosemary) leaf extract, BHT, and tocopherol.

A second sample is prepared according to the first sample, but in this particular sample the vita oils include 1 to 1 ratio of *Helianthus annus* (sunflower) seed oil and *Persea gratissima* (avocado) oil, and the vita oils are at least 5% of the total weight of the skin peel formulation. The remainder of the sample include effective amounts of the following: capric/caprylic triglyceride, dimethyl isosorbide, *Sesamum indicum, Macadamia ternifolia* seed oil, rosa moschata seed oil, squalane, *Rosmarinus officinalis* (rosemary) leaf extract, BHT, and tocopherol. A third sample is prepared according to the second sample wherein squalane in this third sample is at least 1% of the total weight of the skin peel formulation. A fourth sample is prepared according to the second sample, wherein the *Sesamum indicum* is at least 3% of the total weight of the skin peel formulation.

A fifth sample is prepared according to the first sample, with squalane in this sample is at least 1% of the total weight of the skin peel formulation. The remainder of the fifth sample include effective amounts of the following: vita oils including *Helianthus annus* (sunflower) seed oil and *Persea gratissima*, capric/caprylic triglyceride, dimethyl isosorbide, *Sesamum indicum*, macadamia ternifolia seed oil, rosa moschata seed oil, *Rosmarinus officinalis* (rosemary) leaf extract, BHT, and tocopherol. A sixth sample is prepared according to the fifth sample, wherein the *Sesamum indicum* is at least 3% of the total weight of the skin peel formulation.

A seventh sample is prepared according to the first sample, but *Sesamum indicum* is at least 3% of the total weight of the skin peel formulation. The remainder of the seventh sample include effective amounts of the following: vita oils including *Helianthus annus* (sunflower) seed oil and *Persea gratissima*, capric/caprylic triglyceride, dimethyl isosorbide, squalane, *Macadamia ternifolia* seed oil, rosa moschata seed oil, *Rosmarinus officinalis* (rosemary) leaf extract, BHT, and tocopherol. An eighth sample is prepared according to the seventh sample, wherein the squalane is at least 1% of the total weight of the skin peel formulation.

Example 2-10% Vitamin A and 20% Vitamin C

A first sample of a skin peel formulation is prepared using cosmetically acceptable components, where the skin peel formulation includes at least 10% vitamin A and at least 20% vitamin C in oil soluble form. The vitamin A is in the form of retinol, while the vitamin C is tetrahexyldecyl ascorbate in oil soluble form. The remaining weight percentage of the sample include effective amounts of vita oils including *Helianthus annus* (sunflower) seed oil, *Persea gratissima* (avocado) oil, capric/caprylic triglyceride, dimethyl isosorbide, *Sesamum indicum*, macadamia ternifolia seed oil, rosa moschata seed oil, squalane, *Rosmarinus officinalis* (rosemary) leaf extract, BHT, and tocopherol.

A second sample is prepared according to the first sample, but in this particular sample the vita oils include 1 to 1 ratio of *Helianthus annus* (sunflower) seed oil and *Persea gratissima* (avocado) oil, and the vita oils are at least 5% of the total weight of the skin peel formulation. The remainder of the sample include effective amounts of the following: capric/caprylic triglyceride, dimethyl isosorbide, *Sesamum indicum, Macadamia ternifolia* seed oil, rosa moschata seed oil, squalane, *Rosmarinus officinalis* (rosemary) leaf extract, BHT, and tocopherol. A third sample is prepared according to second sample wherein squalane in this third sample is at least 1% of the total weight of the skin peel formulation. A fourth sample is prepared according to the second sample, wherein the *Sesamum indicum* is at least 3% of the total weight of the skin peel formulation.

A fifth sample is prepared according to the first sample, but squalane in this sample is at least 1% of the total weight of the skin peel formulation. The remainder of the fifth sample include effective amounts of the following: vita oils including *Helianthus annus* (sunflower) seed oil and *Persea gratissima*, capric/caprylic triglyceride, dimethyl isosorbide, *Sesamum indicum*, macadamia ternifolia seed oil, rosa moschata seed oil, *Rosmarinus officinalis* (rosemary) leaf extract, BHT, and tocopherol. A sixth sample is prepared according to the fifth sample, wherein the *Sesamum indicum* is at least 3% of the total weight of the skin peel formulation.

A seventh sample is prepared according to the first sample, but *Sesamum indicum* is at least 3% of the total weight of the skin peel formulation. The remainder of the seventh sample include effective amounts of the following: vita oils including *Helianthus annus* (sunflower) seed oil and *Persea gratissima*, capric/caprylic triglyceride, dimethyl isosorbide, squalane, *Macadamia ternifolia* seed oil, rosa moschata seed oil, *Rosmarinus officinalis* (rosemary) leaf extract, BHT, and tocopherol. An eighth sample is prepared according to the seventh sample, wherein the squalane is at least 1% of the total weight of the skin peel formulation.

Example 3

A first group having a first set of eight samples of a skin peel formulation are prepared using cosmetically acceptable components, where the skin peel formulation of each set of samples includes vitamin C in the form of tetrahexyldecyl ascorbate in oil soluble form. The tetrahexyldecyl ascorbate in all eight samples is present in an amount of about 15% of the total weight of the skin peel formulation. Each of the eight samples further includes vitamin A in the form of retinol. Each of the eight samples has a retinol content of the total weight of the skin peel formulation being one of the following ranges 5% to 10%, 6% to 11%, 6% to 12%, 8% to 13%, 10% to 15%, 5% to 20%, and 10% to 20%. The remaining weight percentage of the eight samples of the first group include effective amounts of vita oils including *Helianthus annus* (sunflower) seed oil, *Persea gratissima* (avocado) oil, capric/caprylic triglyceride, dimethyl isosorbide, *Sesamum indicum*, macadamia ternifolia seed oil, rosa moschata seed oil, squalane, *Rosmarinus officinalis* (rosemary) leaf extract, BHT, and tocopherol.

A second set of eight samples of the first group are prepared according to the first set of eight samples, but in this particular second set of eight samples the vita oils include 1 to 1 ratio of *Helianthus annus* (sunflower) seed oil and persea gratissima (avocado) oil, and the vita oils are at least 5% of the total weight of the skin peel formulation. The remainder of the sample include effective amounts of the following: capric/caprylic triglyceride, dimethyl isosorbide, *Sesamum indicum, Macadamia ternifolia* seed oil, rosa moschata seed oil, squalane, *Rosmarinus officinalis* (rosemary) leaf extract, BHT, and tocopherol. A third set of eight samples of the first group are prepared according to the second set of eight samples, wherein squalane in all eights samples of the third set is at least 1% of the total weight of the skin peel formulation. A fourth set of eight samples of the first group are prepared according to the second set of eight samples, wherein the *Sesamum indicum* in all eight samples is at least 3% of the total weight of the skin peel formulation.

A fifth set of eight samples of the first group are prepared according to the eight samples of the first set of the first group, but squalane in each of the eight samples is at least 1% of the total weight of the skin peel formulation. The remainder of the third set of eight samples include effective amounts of the following: vita oils including *Helianthus annus* (sunflower) seed oil and persea gratissima, capric/caprylic triglyceride, dimethyl isosorbide, *Sesamum indicum, Macadamia ternifolia* seed oil, rosa moschata seed oil, *Rosmarinus officinalis* (rosemary) leaf extract, BHT, and tocopherol. A sixth set of eight samples of the first group is prepared according to the fifth set of eight samples, wherein the *Sesamum indicum* is at least 3% of the total weight of the skin peel formulation.

A seventh set of eight samples of the first group is prepared according to the eight samples of the first set of the first group, but *Sesamum indicum* is at least 3% of the total weight of the skin peel formulation. The remainder of the seventh set of eight samples of the first group include effective amounts of the following: vita oils including *Helianthus annus* (sunflower) seed oil and *Persea gratissima*, capric/caprylic triglyceride, dimethyl isosorbide, squalane, *Macadamia ternifolia* seed oil, rosa moschata seed oil, *Rosmarinus officinalis* (rosemary) leaf extract, BHT, and tocopherol. An eighth set of eight samples of the first group is prepared according to the seventh set of eight samples of the first group, wherein the squalane is at least 1% of the total weight of the skin peel formulation.

Example 4

A first group having a first set eight samples of a skin peel formulation are prepared using cosmetically acceptable components, where the skin peel formulation of each set of samples includes vitamin C in the form of tetrahexyldecyl ascorbate in oil soluble form. The tetrahexyldecyl ascorbate in all eight samples is present in an amount of about 10% of the total weight of the skin peel formulation. Each of the eight samples further includes vitamin A in the form of retinol. Each of the eight samples has a retinol content of the total weight of the skin peel formulation being one of the following ranges 5% to 10%, 6% to 11%, 6% to 12%, 8% to 13%, 10% to 15%, 5% to 20%, and 10% to 20%. The remaining weight percentage of the eight samples of the first group include effective amounts of vita oils including *Helianthus annus* (sunflower) seed oil, *Persea gratissima* (avocado) oil, capric/caprylic triglyceride, dimethyl isosorbide, *Sesamum indicum*, macadamia ternifolia seed oil, rosa moschata seed oil, squalane, *Rosmarinus officinalis* (rosemary) leaf extract, BHT, and tocopherol.

A second set of eight samples of the first group are prepared according to the first set of eight samples, but in this particular second set of eight samples the vita oils include 1 to 1 ratio of *Helianthus annus* (sunflower) seed oil and persea gratissima (avocado) oil, and the vita oils are at least 5% of the total weight of the skin peel formulation. The remainder of the sample include effective amounts of the following: capric/caprylic triglyceride, dimethyl isosorbide, *Sesamum indicum, Macadamia ternifolia* seed oil, rosa moschata seed oil, squalane, *Rosmarinus officinalis* (rosemary) leaf extract, BHT, and tocopherol. A third set of eight samples of the first group are prepared according to the second set of eight samples, wherein squalane in all eights samples of the third set is at least 1% of the total weight of the skin peel formulation. A fourth set of eight samples of the first group are prepared according to the second set of eight samples, wherein the *Sesamum indicum* in all eight samples is at least 3% of the total weight of the skin peel formulation.

A fifth set of eight samples of the first group are prepared according to the eight samples of the first set of the first group, but squalane in each of the eight samples is at least 1% of the total weight of the skin peel formulation. The remainder of the third set of eight samples include effective amounts of the following: vita oils including *Helianthus annus* (sunflower) seed oil and persea gratissima, capric/caprylic triglyceride, dimethyl isosorbide, *Sesamum indicum, Macadamia ternifolia* seed oil, rosa moschata seed oil, *Rosmarinus officinalis* (rosemary) leaf extract, BHT, and tocopherol. A sixth set of eight samples of the first group is prepared according to the fifth set of eight samples, wherein the *Sesamum indicum* is at least 3% of the total weight of the skin peel formulation.

A seventh set of eight samples of the first group is prepared according to the eight samples of the first set of the first group, but *Sesamum indicum* is at least 3% of the total weight of the skin peel formulation. The remainder of the seventh set of eight samples of the first group include effective amounts of the following: vita oils including *Helianthus annus* (sunflower) seed oil and *Persea gratissima*, capric/caprylic triglyceride, dimethyl isosorbide, squalane, *Macadamia ternifolia* seed oil, rosa moschata seed oil, *Rosmarinus officinalis* (rosemary) leaf extract, BHT, and tocopherol. An eighth set of eight samples of the first group is prepared according to the seventh set of eight samples of the first group, wherein the squalane is at least 1% of the total weight of the skin peel formulation.

Example 5

A first group having a first set eight samples of a skin peel formulation are prepared using cosmetically acceptable components, where the skin peel formulation of each set of samples includes vitamin C in the form of tetrahexyldecyl ascorbate in oil soluble form. The tetrahexyldecyl ascorbate in all eight samples is present in an amount of about 30% the total weight of the skin peel formulation. Each of the eight samples further includes vitamin A in the form of retinol. Each of the eight samples has a retinol content of the total weight of the skin peel formulation being one of the following ranges 5% to 10%, 6% to 11%, 6% to 12%, 8% to 13%, 10% to 15%, 5% to 20%, and 10% to 20%. The remaining weight percentage of the eight samples of the first group include effective amounts of vita oils including *Helianthus annus* (sunflower) seed oil, *Persea gratissima* (avocado) oil, capric/caprylic triglyceride, dimethyl isosorbide, *Sesamum indicum*, macadamia ternifolia seed oil, rosa moschata seed oil, squalane, *Rosmarinus officinalis* (rosemary) leaf extract, BHT, and tocopherol.

A second set of eight samples of the first group are prepared according to the first set of eight samples, but in this particular second set of eight samples the vita oils include 1 to 1 ratio of *Helianthus annus* (sunflower) seed oil and persea gratissima (avocado) oil, and the vita oils are at least 5% of the total weight of the skin peel formulation. The remainder of the sample include effective amounts of the following: capric/caprylic triglyceride, dimethyl isosorbide, *Sesamum indicum, Macadamia ternifolia* seed oil, rosa moschata seed oil, squalane, *Rosmarinus officinalis* (rosemary) leaf extract, BHT, and tocopherol. A third set of eight samples of the first group are prepared according to the second set of eight samples, wherein squalane in all eights samples of the third set is at least 1% of the total weight of the skin peel formulation. A fourth set of eight samples of the first group are prepared according to the second set of eight samples, wherein the *Sesamum indicum* in all eight samples is at least 3% of the total weight of the skin peel formulation.

A fifth set of eight samples of the first group are prepared according to the eight samples of the first set of the first group, but squalane in each of the eight samples is at least 1% of the total weight of the skin peel formulation. The remainder of the third set of eight samples include effective amounts of the following: vita oils including *Helianthus annus* (sunflower) seed oil and persea gratissima, capric/caprylic triglyceride, dimethyl isosorbide, *Sesamum indicum, Macadamia ternifolia* seed oil, rosa moschata seed oil, *Rosmarinus officinalis* (rosemary) leaf extract, BHT, and tocopherol. A sixth set of eight samples of the first group is prepared according to the fifth set of eight samples, wherein the *Sesamum indicum* is at least 3% of the total weight of the skin peel formulation.

A seventh set of eight samples of the first group is prepared according to the eight samples of the first set of the first group, but *Sesamum indicum* is at least 3% of the total weight of the skin peel formulation. The remainder of the seventh set of eight samples of the first group include effective amounts of the following: vita oils including *Helianthus annus* (sunflower) seed oil and *Persea gratissima*, capric/caprylic triglyceride, dimethyl isosorbide, squalane, *Macadamia ternifolia* seed oil, rosa moschata seed oil, *Rosmarinus officinalis* (rosemary) leaf extract, BHT, and tocopherol. An eighth set of eight samples of the first group is prepared according to the seventh set of eight samples of the first group, wherein the squalane is at least 1% of the total weight of the skin peel formulation.

Example 6

A first group having a first set eight samples of a skin peel formulation are prepared using cosmetically acceptable components, where the skin peel formulation of each set of samples includes vitamin C in the form of tetrahexyldecyl ascorbate in oil soluble form. The tetrahexyldecyl ascorbate in all eight samples is present in a range between about 20% to about 30% the total weight of the skin peel formulation. Each of the eight samples further includes vitamin A in the form of retinol. Each of the eight samples has a retinol content of the total weight of the skin peel formulation being one of the following ranges 5% to 10%, 6% to 11%, 6% to 12%, 8% to 13%, 10% to 15%, 5% to 20%, and 10% to 20%. The remaining weight percentage of the eight samples of the first group include effective amounts of vita oils including *Helianthus annus* (sunflower) seed oil, *Persea gratissima* (avocado) oil, capric/caprylic triglyceride, dimethyl isosorbide, *Sesamum indicum, Macadamia ternifolia* seed oil, rosa moschata seed oil, squalane, *Rosmarinus officinalis* (rosemary) leaf extract, BHT, and tocopherol.

A second set of eight samples of the first group are prepared according to the first set of eight samples, but in this particular second set of eight samples the vita oils include 1 to 1 ratio of *Helianthus annus* (sunflower) seed oil and persea gratissima (avocado) oil, and the vita oils are at least 5% of the total weight of the skin peel formulation. The remainder of the sample include effective amounts of the following: capric/caprylic triglyceride, dimethyl isosorbide, *Sesamum indicum, Macadamia ternifolia* seed oil, rosa moschata seed oil, squalane, *Rosmarinus officinalis* (rosemary) leaf extract, BHT, and tocopherol. A third set of eight samples of the first group are prepared according to the second set of eight samples, wherein squalane in all eights samples of the third set is at least 1% of the total weight of the skin peel formulation. A fourth set of eight samples of the first group are prepared according to the second set of eight samples, wherein the *Sesamum indicum* in all eight samples is at least 3% of the total weight of the skin peel formulation.

A fifth set of eight samples of the first group are prepared according to the eight samples of the first set of the first group, but squalane in each of the eight samples is at least 1% of the total weight of the skin peel formulation. The remainder of the third set of eight samples include effective amounts of the following: vita oils including *Helianthus annus* (sunflower) seed oil and persea gratissima, capric/caprylic triglyceride, dimethyl isosorbide, *Sesamum indicum, Macadamia ternifolia* seed oil, rosa moschata seed oil, *Rosmarinus officinalis* (rosemary) leaf extract, BHT, and tocopherol. A sixth set of eight samples of the first group is prepared according to the fifth set of eight samples, wherein the *Sesamum indicum* is at least 3% of the total weight of the skin peel formulation.

A seventh set of eight samples of the first group is prepared according to the eight samples of the first set of the first group, but *Sesamum indicum* is at least 3% of the total weight of the skin peel formulation. The remainder of the seventh set of eight samples of the first group include effective amounts of the following: vita oils including *Helianthus annus* (sunflower) seed oil and *Persea gratissima*, capric/caprylic triglyceride, dimethyl isosorbide, squalane, *Macadamia ternifolia* seed oil, rosa moschata seed oil, *Rosmarinus officinalis* (rosemary) leaf extract, BHT, and tocopherol. An eighth set of eight samples of the first group is prepared according to the seventh set of eight samples of the first group, wherein the squalane is at least 1% of the total weight of the skin peel formulation.

Example 7

A first group having a first set eight samples of a skin peel formulation are prepared using cosmetically acceptable components, where the skin peel formulation of each set of samples includes vitamin C in the form of tetrahexyldecyl ascorbate in oil soluble form. The tetrahexyldecyl ascorbate in all eight samples is present in a range between about 25% to about 30% the total weight of the skin peel formulation. Each of the eight samples further includes vitamin A in the form of retinol. Each of the eight samples further includes vitamin A in the form of retinol. Each of the eight samples has a retinol content of the total weight of the skin peel formulation being one of the following ranges 5% to 10%, 6% to 11%, 6% to 12%, 8% to 13%, 10% to 15%, 5% to 20%, and 10% to 20%. The remaining weight percentage of the eight samples of the first group include effective amounts of vita oils including *Helianthus annus* (sunflower) seed oil, *Persea gratissima* (avocado) oil, capric/caprylic triglyceride, dimethyl isosorbide, *Sesamum indicum*, macadamia ternifolia seed oil, rosa moschata seed oil, squalane, *Rosmarinus officinalis* (rosemary) leaf extract, BHT, and tocopherol.

A second set of eight samples of the first group are prepared according to the first set of eight samples, but in this particular second set of eight samples the vita oils include 1 to 1 ratio of *Helianthus annus* (sunflower) seed oil and persea gratissima (avocado) oil, and the vita oils are at least 5% of the total weight of the skin peel formulation. The remainder of the sample include effective amounts of the following: capric/caprylic triglyceride, dimethyl isosorbide, *Sesamum indicum, Macadamia ternifolia* seed oil, rosa moschata seed oil, squalane, *Rosmarinus officinalis* (rosemary) leaf extract, BHT, and tocopherol. A third set of eight samples of the first group are prepared according to the second set of eight samples, wherein squalane in all eights samples of the third set is at least 1% of the total weight of the skin peel formulation. A fourth set of eight samples of the first group are prepared according to the second set of eight samples, wherein the *Sesamum indicum* in all eight samples is at least 3% of the total weight of the skin peel formulation.

A fifth set of eight samples of the first group are prepared according to the eight samples of the first set of the first group, but squalane in each of the eight samples is at least 1% of the total weight of the skin peel formulation. The remainder of the third set of eight samples include effective amounts of the following: vita oils including *Helianthus annus* (sunflower) seed oil and persea gratissima, capric/caprylic triglyceride, dimethyl isosorbide, *Sesamum indicum, Macadamia ternifolia* seed oil, rosa moschata seed oil, *Rosmarinus officinalis* (rosemary) leaf extract, BHT, and tocopherol. A sixth set of eight samples of the first group is prepared according to the fifth set of eight samples, wherein the *Sesamum indicum* is at least 3% of the total weight of the skin peel formulation.

A seventh set of eight samples of the first group is prepared according to the eight samples of the first set of the first group, but *Sesamum indicum* is at least 3% of the total weight of the skin peel formulation. The remainder of the seventh set of eight samples of the first group include effective amounts of the following: vita oils including *Helianthus annus* (sunflower) seed oil and *Persea gratissima*, capric/caprylic triglyceride, dimethyl isosorbide, squalane, *Macadamia ternifolia* seed oil, rosa moschata seed oil, *Rosmarinus officinalis* (rosemary) leaf extract, BHT, and tocopherol. An eighth set of eight samples of the first group is prepared according to the seventh set of eight samples of the first group, wherein the squalane is at least 1% of the total weight of the skin peel formulation.

Example 8

A first group having a first set eight samples of a skin peel formulation are prepared using cosmetically acceptable components, where the skin peel formulation of each set of samples includes vitamin C in the form of tetrahexyldecyl ascorbate in oil soluble form. The tetrahexyldecyl ascorbate in all eight samples is present in an amount of about 26% of the total weight of the skin peel formulation. Each of the eight samples further includes vitamin A in the form of retinol. Each of the eight samples has a retinol content of the total weight of the skin peel formulation being one of the following ranges 5% to 10%, 6% to 11%, 6% to 12%, 8% to 13%, 10% to 15%, 5% to 20%, and 10% to 20%. The remaining weight percentage of the eight samples of the first group include effective amounts of vita oils including *Helianthus annus* (sunflower) seed oil, *Persea gratissima* (avocado) oil, capric/caprylic triglyceride, dimethyl isosorbide, *Sesamum indicum*, macadamia ternifolia seed oil, rosa moschata seed oil, squalane, *Rosmarinus officinalis* (rosemary) leaf extract, BHT, and tocopherol.

A second set of eight samples of the first group are prepared according to the first set of eight samples, but in this particular second set of eight samples the vita oils include 1 to 1 ratio of *Helianthus annus* (sunflower) seed oil and persea gratissima (avocado) oil, and the vita oils are at least 5% of the total weight of the skin peel formulation. The remainder of the sample include effective amounts of the following: capric/caprylic triglyceride, dimethyl isosorbide, *Sesamum indicum, Macadamia ternifolia* seed oil, rosa moschata seed oil, squalane, *Rosmarinus officinalis* (rosemary) leaf extract, BHT, and tocopherol. A third set of eight samples of the first group are prepared according to the second set of eight samples, wherein squalane in all eights samples of the third set is at least 1% of the total weight of the skin peel formulation. A fourth set of eight samples of the first group are prepared according to the second set of eight samples, wherein the *Sesamum indicum* in all eight samples is at least 3% of the total weight of the skin peel formulation.

A fifth set of eight samples of the first group are prepared according to the eight samples of the first set of the first group, but squalane in each of the eight samples is at least 1% of the total weight of the skin peel formulation. The remainder of the third set of eight samples include effective amounts of the following: vita oils including *Helianthus annus* (sunflower) seed oil and persea gratissima, capric/caprylic triglyceride, dimethyl isosorbide, *Sesamum indicum, Macadamia ternifolia* seed oil, rosa moschata seed oil, *Rosmarinus officinalis* (rosemary) leaf extract, BHT, and tocopherol. A sixth set of eight samples of the first group is prepared according to the fifth set of eight samples, wherein the *Sesamum indicum* is at least 3% of the total weight of the skin peel formulation.

A seventh set of eight samples of the first group is prepared according to the eight samples of the first set of the first group, but *Sesamum indicum* is at least 3% of the total weight of the skin peel formulation. The remainder of the seventh set of eight samples of the first group include effective amounts of the following: vita oils including *Helianthus annus* (sunflower) seed oil and *Persea gratissima*, capric/caprylic triglyceride, dimethyl isosorbide, squalane, *Macadamia ternifolia* seed oil, rosa moschata seed oil, *Rosmarinus officinalis* (rosemary) leaf extract, BHT, and tocopherol. An eighth set of eight samples of the first group is prepared according to the seventh set of eight samples of the first group, wherein the squalane is at least 1% of the total weight of the skin peel formulation.

Method of Application of the Skin Peel Formulation

All of the samples set forth in Examples 1 to 8 above are used in accordance with a method of applying a skin peel formulation or product according to the present invention. The method includes providing a skin peel formulation is one of the samples prepared according to Examples 1 to 8 above. The skin peel formulation or product is suitable for topical application to a region of the body where treatment is needed.

The next step involves applying the skin peel formulation to a region of the body by first applying water to the region of the body, and then applying the skin peel formulation. While applying water is specifically described it is within the scope of the invention for the skin peel formulation to be applied without any kind of pre-treatment of the region of the body. Also, more specifically the step of applying the skin peel formulation is done without any acid pre-treatments to the region of the body. The acid solutions that are not applied include any acid or combination of acids that sufficiently exfoliate the superficial dermis and/or epidermis. The acidic solution not applied specifically include one or more of lactic acid, salicylic acid, resorcinol, glycolic acid, malic acid, mandelic acid, citric acid, Trichloroacetic acid (TCA), phenol, tartaric acid, Isoceteth-20, or a combination thereof. The region of the body is typically the face or neck area but can be any area of the body where skin peeling is desired.

The next step includes waiting at least 25 days before applying the skin peel formulation again to the region of the body without any pre-treatment to the region of the body. The skin peel formulation of the present invention in one embodiment uses a single application method and does not require daily application or pre-treatments with other substances, aside from water, which is optional, prior to applying the skin peel formulation. In another method of the invention the step of applying the skin peel formulation further includes repeating the step of applying the skin peel formulation for not more than 3 successive days prior to the step of waiting at least 25 days. This particular method is used when a deeper exfoliation of the skin is desired or if a user has a particular skin type that needs a greater dosage of the skin peel formulation to achieve the desired exfoliation.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A method of applying a skin peel formulation comprising the steps of:
   providing a skin peel formulation containing at least 10% of the total weight of the skin peel formulation being vitamin A, wherein the vitamin A is retinol and at least 20% of the total weight of the skin peel formulation being vitamin C, wherein the vitamin C is tetrahexyldecyl ascorbate in oil soluble form;
   applying the skin peel formulation to a region of the body, wherein the step of applying the skin peel formulation is done without any acid pre-treatments to the region of the body, and
   waiting at least 25 days before applying the skin peel formulation again to the region of the body without any pre-treatment to the region of the body.

2. The method of applying a skin peel formulation of claim 1 wherein the step of applying the skin peel formulation excludes all pre-treatments to the regions of the body except the application of water just prior to application of the skin peel formulation.

3. The method of applying the skin peel formulation of claim 1 wherein the step of providing the skin peel formulation further includes providing at least 3% of the total weight of the skin peel formulation being *Sesamum indicum*.

4. The method of applying the skin peel formulation of claim 1 wherein the step of providing the skin peel formulation further includes providing at least 1% of the total weight of the skin peel formulation being squalane.

5. The method of applying the skin peel formulation of claim 1 wherein the step of providing the skin peel formulation further includes providing at least 5% of the total weight of the skin peel formulation being vita oil.

6. The method of applying the skin peel formulation of claim 5 wherein the vita oils include *Helianthus annus* seed oil, *Persea gratissima* oil.

7. The method of applying the skin peel formulation of claim 5 wherein the step of providing the skin peel formulation further includes providing at least 1% of the total weight of the skin peel formulation being squalane.

8. The method of applying the skin peel formulation of claim 1 wherein the step of providing the skin peel formulation consists of providing capric/caprylic triglyceride, retinol, *Helianthus annus* seed oil, *Persea gratissima* oil, dimethyl isosorbide, *Sesamum indicum*, macadamia ternifolia seed oil, rosa moschata seed oil, *Rosmarinus officinalis* leaf extract, BHT, and tocopherol.

9. A method of applying a skin peel formulation comprising the steps of:
   providing a skin peel formulation containing at least 10% of the total weight of the skin peel formulation being vitamin A, at least 3% of the total weight of the skin peel formulation being *Sesamum indicum*, and at least 20% of the total weight of the skin peel formulation being vitamin C, wherein the vitamin C is in oil soluble form;
   applying the skin peel formulation to a region of the body, wherein the step of applying the skin peel formulation is done without any acid pre-treatments to the region of the body, and
   waiting at least 25 days before applying the skin peel formulation again to the region of the body without any pre-treatment to the region of the body.

10. The method of applying a skin peel formulation of claim 9 wherein the step of applying the skin peel formulation excludes all pre-treatments to the regions of the body except the application of water just prior to application of the skin peel formulation.

11. The method of applying the skin peel formulation of claim 9 wherein the step of providing the skin peel formulation further includes providing at least 1% of the total weight of the skin peel formulation being squalane.

12. The method of applying the skin peel formulation of claim 9 wherein the step of providing the skin peel formulation further includes providing at least 5% of the total weight of the skin peel formulation being vita oil.

13. The method of applying the skin peel formulation of claim 12 wherein the vita oils include *Helianthus annus* seed oil, *Persea gratissima* oil.

14. The method of applying the skin peel formulation of claim 12 wherein the step of providing the skin peel formulation further includes providing at least 1% of the total weight of the skin peel formulation being squalane.

15. The method of applying the skin peel formulation of claim 9 wherein the step of providing the skin peel formulation consists of providing capric/caprylic triglyceride, retinol, *Helianthus annus* seed oil, *Persea gratissima* oil, dimethyl isosorbide, *Sesamum indicum, Macadamia ternifolia* seed oil, rosa moschata seed oil, *Rosmarinus officinalis* leaf extract, BHT, and tocopherol.

16. The method of applying the skin peel formulation of claim 9 wherein the vitamin A is retinol and the vitamin C is tetrahexyldecyl ascorbate.

\* \* \* \* \*